United States Patent
Collins et al.

(10) Patent No.: US 9,332,955 B2
(45) Date of Patent: May 10, 2016

(54) ADAPTIVE DUAL-PASS TARGETED RECONSTRUCTION AND ACQUISITION

(71) Applicant: KONINKLIJKE PHILIPS N.V., Eindhoven (NL)

(72) Inventors: John Patrick Collins, Cleveland Heights, OH (US); Chi-Hua Tung, Aurora, OH (US); Bin Zhang, Cleveland, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 112 days.

(21) Appl. No.: 14/348,905

(22) PCT Filed: Sep. 21, 2012

(86) PCT No.: PCT/IB2012/055007
§ 371 (c)(1),
(2) Date: Apr. 1, 2014

(87) PCT Pub. No.: WO2013/050897
PCT Pub. Date: Apr. 11, 2013

(65) Prior Publication Data
US 2014/0249408 A1    Sep. 4, 2014

Related U.S. Application Data

(60) Provisional application No. 61/542,977, filed on Oct. 4, 2011.

(51) Int. Cl.
*A61B 6/00* (2006.01)
*A61B 6/03* (2006.01)

(52) U.S. Cl.
CPC ............... *A61B 6/5235* (2013.01); *A61B 6/032* (2013.01); *A61B 6/037* (2013.01); *A61B 6/545* (2013.01); *A61B 6/4417* (2013.01)

(58) Field of Classification Search
CPC ...... A61B 6/032; A61B 6/037; A61B 6/4417; A61B 6/5235; A61B 6/545
See application file for complete search history.

(56) References Cited

U.S. PATENT DOCUMENTS

| | | | |
|---|---|---|---|
| 7,737,405 B2 | 6/2010 | Watson et al. | |
| 2009/0012383 A1* | 1/2009 | Virtue | A61B 6/032 600/407 |

(Continued)

FOREIGN PATENT DOCUMENTS

CN    101933836    5/2011

OTHER PUBLICATIONS

Townsend, D. W., et al.; Continuous bed motion acquisition for an LSO PET/CT scanner; 2004; IEEE Nuclear Science Symposium Conference Record; pp. 2383-2387.

(Continued)

*Primary Examiner* — Mark Remaly

(57) ABSTRACT

A hybrid imaging system includes a first imaging system configured to acquire anatomical data of a first field of view of an anatomical structure. A second imaging system configured to acquire functional data of the anatomical structure, the second imaging system acquiring functional data in a two-pass list-mode acquisition scheme. A reconstruction processor configured to reconstruct the functional data based on attenuation data into an attenuation corrected image and reconstruct the anatomical data into one or more high resolution images of one or more regions of interest.

17 Claims, 2 Drawing Sheets

(56) References Cited

U.S. PATENT DOCUMENTS

| | | |
|---|---|---|
| 2009/0324042 A1 | 12/2009 | Laurance et al. |
| 2010/0067765 A1 | 3/2010 | Buther et al. |
| 2010/0329531 A1 | 12/2010 | Martinez-Moller et al. |
| 2011/0079722 A1 | 4/2011 | Gagnon |
| 2011/0105887 A1 | 5/2011 | Gagnon et al. |

OTHER PUBLICATIONS

Zhou, J., et al.; Adaptive Imaging for Lesion Detection Using a Zoom-in PET System; 2011; IEEE Trans. on Medical Imaging; 30(1)119-130.

* cited by examiner

ADAPTIVE DUAL-PASS TARGETED RECONSTRUCTION AND ACQUISITION

CROSS REFERENCE TO RELATED APPLICATIONS

This application is a national filing of PCT application Serial No. PCT/IB2012/055007, filed Sep. 21, 2012, published as WO2013/050897A1 on Apr. 11, 2013, which claims the benefit of U.S. provisional application Ser. No. 61/542, 977 filed Oct. 4, 2011, which is incorporated herein by reference.

The present application relates to diagnostic imaging systems and methods. It finds particular application in improving image acquisition reconstruction and accelerating workflow of multi-modality imaging systems combining MRI, CT, and one of PET or SPECT, but may find applicability in other diagnostic or treatment systems.

In multi-modality or hybrid imaging systems, two different sensing modalities, such as nuclear imaging scanners like PET or SPECT coupled with an anatomical imaging scanner such as CT, XCT, MRI, and the like are used to locate or measure different constituents in the object space. For example, the PET and SPECT scanners create functional images indicative of metabolic activity in the body, rather than creating images of surrounding anatomy. CT and MRI scanners allow doctors to see internal structures such as bones or spine, and soft tissue structures like the brain, vasculature, joints, and the like within the human body; each with their individual advantages and disadvantages for a clinical question at hand.

A patient receives a dose of a radiopharmaceutical. The pharmaceutical is e.g. carried through the blood and concentrates in one or more target organs or regions and emits radiation. During a nuclear scanning procedure, the emitted radiation is detected by the system and reconstructed into an image of the distribution of the radiopharmaceutical in the patient. The image can show the circulatory system and/or the relative absorption of the radiopharmaceutical in various regions or organs. Cancerous tumors, for example, absorb significant quantities of glucose containing radiopharmaceuticals. Integration of anatomical data from an anatomical scanning procedure with the metabolic data from the nuclear scanning procedure in a hybrid image gives physicians visual information to determine if disease is present, the location and extent of disease, and track how rapidly it is spreading. Hybrid imaging systems are particularly helpful in difficult-to-treat regions (e.g. head and neck area, mediastinum, post-surgical abdomen) and localization of the treatment area for the patients receiving radiation therapy or chemotherapy.

Anatomical imaging data can also be used for attenuation correction to further enhance nuclear imaging data. Attenuation correction in traditional nuclear imaging systems can involve a transmission scan in which an external radioactive transmission source rotates around a field of view (FOV) and measures the attenuation through the examination region. CT images are also used for attenuation correction. The hybrid imaging system uses the anatomical data to construct an attenuation map of density differences throughout the body and to correct for absorption of emitted photons.

Typically, the patient is first imaged with a high resolution, high dose CT imaging system before starting the nuclear imaging scanning procedure. In some systems, a high resolution MRI imaging system is used. The typical procedure on a hybrid imaging system is to acquire a full diagnosis high resolution CT image, spanning the full region of the patient to be examined. After the CT image is generated, a nuclear image of the examined region is generated. The CT image is registered to the nuclear image and used for attenuation correction when reconstructing the nuclear image. Additionally, it is common to perform multiple studies of a patient with the same injection; for example, a whole-body study and a targeted study. Multiple studies are performed because often the tumor or regions of interest are not localized to only the region of the targeted study.

Clinical experience and the preferences of physicians is used to select how data is acquired and reconstructed rather than objective information about a particular patient. The variation of acquisition and reconstruction parameters among patients depends on a few basic predetermined categories such as anatomic region (brain, heart, lungs, general body), age (infant or adult), weight or BMI (to distinguish bariatric and normal cases), and the like. These categories have few, often only two, clusters each and the categorization is rigid and abrupt because of the simple binary classification scheme. Whole-body studies typically use the same acquisition and reconstruction parameters for the entire study. Furthermore, whole-body acquisitions are sometimes augmented by another study (such as a higher resolution head study) that involves a separate acquisition and reconstruction.

The present application provides a new and improved apparatus and method which overcomes the above-referenced problems and others.

In accordance with one aspect, a hybrid imaging system is provided. The hybrid imaging system including a first imaging system configured to acquire anatomical data of a first field of view of an anatomical structure. A second imaging system configured to acquire functional data of the anatomical structure, the second imaging system acquiring functional data in a two-pass list-mode acquisition scheme. A reconstruction processor configured to reconstruct the functional data based on attenuation data into an attenuation corrected image and reconstruct the anatomical data into one or more high resolution images of one or more regions of interest.

In accordance with another aspect, a method is provided. The method includes acquiring anatomical data of a first field of view of an anatomical structure, acquiring functional data of the first field of view of the anatomical structure, reconstructing the functional data using the data for attenuation correction into an attenuation corrected image, the functional data being acquired in a two-pass list-mode acquisition scheme, acquiring anatomical data in second fields of view which encompass the one or more regions of interest, the second fields of view being smaller than and confined in the first field of view, and reconstructing the anatomical data into one or more high resolution images.

In accordance with another aspect, a hybrid imaging system is provided. The hybrid imaging system includes a CT imaging system configured to acquire attenuation data of a first field of view of an anatomical structure. A PET imaging system is configured to acquire first list mode data in a first pass. A reconstruction processor is configured to reconstruct the first list mode data based on attenuation data into an attenuation corrected image. The PET imaging system further acquires second list mode data in a second pass and the reconstruction processor further reconstructs the attenuation corrected image and the second list mode data into a final attenuation corrected image.

One advantage resides in the utilization of preliminary patient information to drive collection of subsequent patient information.

Another advantage resides in improved workflow.

Another advantage resides in greater imaging efficiency and patient throughput.

Another advantage resides in dose savings.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
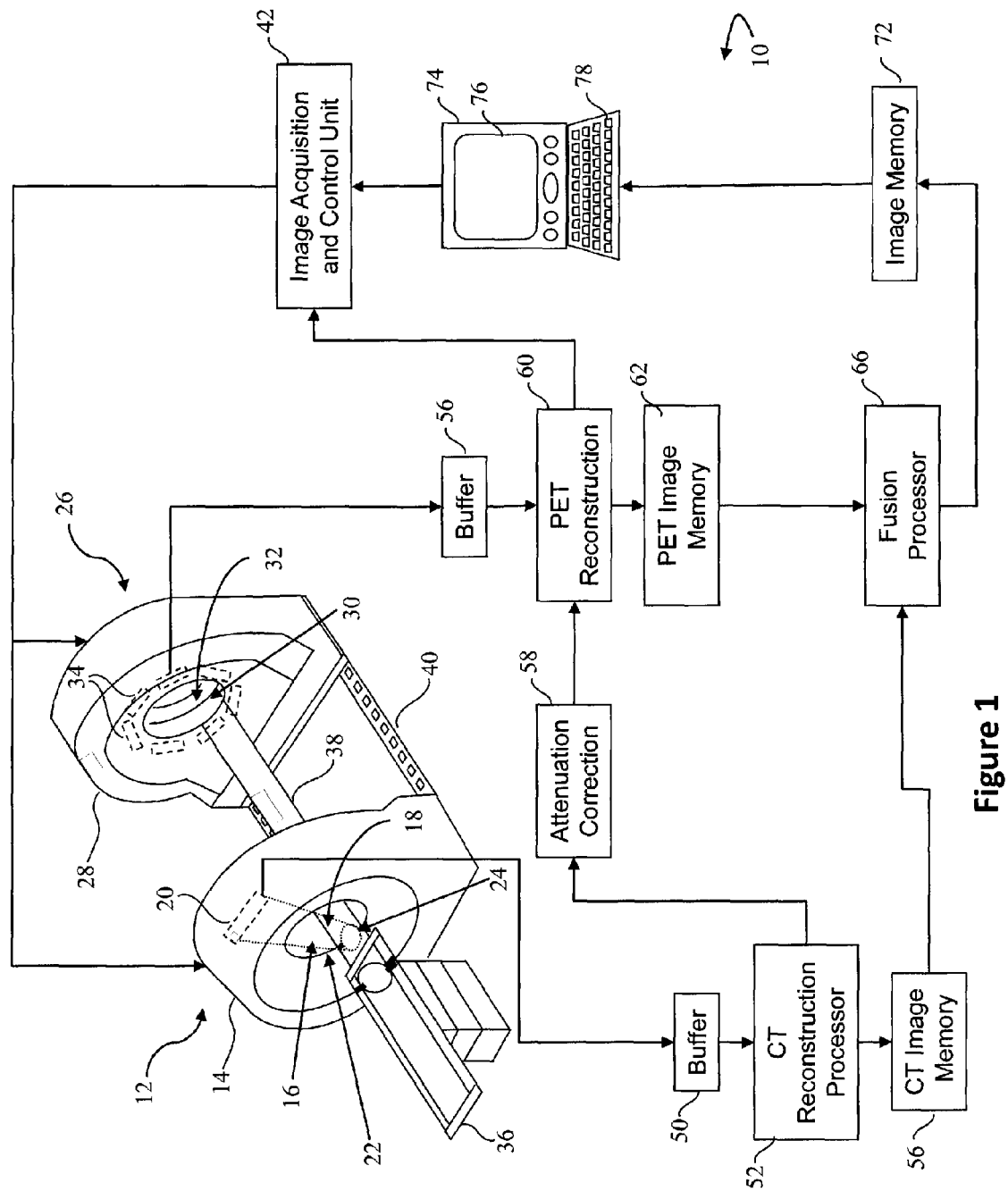
FIG. 1 is a diagrammatic view of combined PET/CT system in accordance with the present application.

FIG. 1 illustrates a hybrid imaging system 10 which implements a workflow that optimizes image quality while minimizing scan length and/or duration. The workflow, described in detail below, is an adaptive two-pass continuous list-mode PET acquisition and reconstruction scheme that is based on the particulars of the study including the isotope type and activity as well as the patient's physiology. The workflow begins with an attenuation correction (AC) scan using a low-dose computer tomography (CT) or a fast magnetic resonance (MR) imaging procedure. A first single Photon Emission Computed Tomography (SPECT) and/or Positron Emission Tomography (PET) reconnaissance scan is performed utilizing a fast continuous list-mode acquisition. Combined with the CT image, the PET reconnaissance scan provides statistical feedback from PET plus anatomical information from CT that can be used to drive a second SPECT or PET scan. The second pass is the "targeted scan", which targets potentially noncontiguous regions thereby potentially reducing the dose required for CT. The regions can be defined purely from empirical data obtained from the reconnaissance scan and CT surview, as well as operator input defining particular regions. The regions (targeted zones) allow the acquisition time to vary by region, acquiring data where and as required. Criteria for determining the time per region can be determined using the noise equivalent count rate (NECR), singles rate, total attenuation, and the like. The actual time required for the second pass can be reduced by reusing the data acquired from the reconnaissance scan. The reconstruction parameters can similarly vary by region. A single study can be used to provide data that would typically require multiple studies. A two-pass approach collects data for a region based on the most demanding requirement for a particular protocol/study yet enables protocols not requiring as much data in a particular region to select the amount of data required.

With reference to FIG. 1, a multimodality imaging system employs at least two different imaging modalities. In the illustrative examples set forth herein, the multi-modality imaging facility employs computed tomography (CT) and positron emission tomography (PET) imaging modalities using a hybrid PET/CT imaging system 10 that includes a CT scanner 12, housed within a first gantry 14. A bore 16 defines a first examination region 18 of the CT scanner 12. An array of radiation detectors 20 is disposed on a rotating gantry 22 configured to receive transmission radiation from an x-ray source 24 disposed opposite the detectors 20 on the rotating gantry 22. The hybrid PET/CT imaging system 10 also includes a PET scanner 26 housed within a second gantry 28 which defines a patient receiving bore 30. A ring of radiation detectors 34 are arranged around the bore 30 to define a second or PET examination region 32.

In the illustrated embodiment, the two gantries 14, 28 are adjacent to one another and share a common patient support 36 that translates along a longitudinal axis between the two examination regions 18, 32 along a patient support track or path 38. A motor or other drive mechanism (not shown) provides the longitudinal movement and vertical adjustments of the support in the examination regions 18, 32. In the illustrated embodiment, the PET gantry 28 translates along a gantry track 40 to reduce the transit time and distance between imaging systems 12, 26. A close arrangement between gantries reduces the likelihood of patient movement and mis-registration errors stemming from increased scan times.

A different type of hybrid PET/CT imaging system, or another type of hybrid imaging system such as a hybrid magnetic resonance MR/PET imaging system or so forth can be provided in addition to or in place of the illustrated hybrid PET/CT imaging system 10. Moreover, multimodality imaging can instead or additionally be provided by one or more standalone imaging systems, such as a standalone low dose CT scanner, C-arm x-ray scanner, a standalone high dose CT scanner, a standalone PET scanner, a standalone MR scanner, a standalone gamma camera configured for SPECT imaging, or so forth. Still further, in some embodiments a single imaging instrument may be configured to provide multimodality imaging. For example, it is contemplated for the multimodality imaging system to include PET and MR systems in a common gantry, PET and a low dose radiation source in a single gantry, PET and CT in a common gantry, and the like.

With continuing reference to FIG. 1, the patient support 36 positions the patient or subject to be imaged into the first examination region 18 and an imaging acquisition and control unit 42 controls an x-ray tube 24 and cooperating x-ray detector array 20 (components disposed in the CT scanner 12) to generate and acquire a surview CT projection data. The acquired surview CT projection data is temporarily stored in a data buffer 50 and reconstructed by a CT reconstruction processor 52 to generate one or more surview CT images that are stored in a CT images memory 56. The CT reconstruction processor 52 also generates information indicative of the radiation attenuation of the patient or subject being examined in the first examination space 18. The attenuation information is generally expressed in Hounsfield Units (HU). An attenuation map is generated from the attenuation information by an attenuation correction unit 58 which is used by a PET reconstruction processor 60 to generate an attenuation corrected PET image representations. Information from the attenuation map is used to correct for errors resulting from non-uniform radiation attenuation characteristics of the patient or subject being examined (e.g., the presence of bones in a human patient).

In similar fashion, the patient support 36 positions the patient or subject to be imaged into the second examination region 32 and the imaging acquisition and control unit 42 operates PET radiation detectors 34 to acquire PET line-of-response data (optionally including time-of-flight localization). For example, a triggering and time stamp processor monitors each detector for an energy spike, e.g., integrated area under the pulse, characteristic of the energy of the gamma rays generated by the radiopharmaceutical. The triggering and time stamp processor checks a clock and stamps each detected gamma ray event with a time of leading edge receipt and, in a time of flight scanner, a time of flight (TOF). In PET imaging, the time stamp, energy estimate, and a location of the detector are first used by an event verification processor to determine whether there is a coincident event. Accepted pairs of coincident events define lines of response (LORs). Once an event pair is verified by the event verification processor, the LOR is passed to an event storage buffer with their time stamps and end point detectors locations are stored in the event storage buffer 56 as line-of-response data. The PET line-of-response data is temporarily stored in a data buffer 56 and reconstructed by a PET reconstruction processor 60 to generate one or more PET images that are stored in a PET image memory 62. The attenuation map generated by the attenuation correction unit 58 is used by a PET image reconstruction processor 60 to generate an attenuation corrected PET image representation from the PET data. In the case of PET imaging, a suitable positron-emitting radiopharmaceutical is administered to the subject prior to the PET data acquisition. The emitted positrons undergo positron/electron annihilation with each such annihilation event generating 511 keV gamma rays travelling in opposite directions, thus defining a line-of-response.

Specifically, the imaging acquisition and control unit 42 controls the PET radiation detectors 34 to operate in an adaptive two-pass continuous list-mode PET acquisition and reconstruction scheme that is based on the particulars of the study including the isotope type and activity as well as the patient's physiology. The two-pass continuous list-mode PET acquisition includes a first reconnaissance scan while the patient support 36 is being moved into the second examination region 32 and a targeted scan while the patient support 36 is being positioned moved out of the second examination region 32. During the reconnaissance scan, the imaging acquisition and control unit 42 controls the PET radiation detectors 34 collect the PET line-of-response data in a fast continuous list-mode acquisition manner. The PET line-of-response data is combined with the surview CT image to provide functional and anatomical information that is used to drive the targeted scan. Specifically, the PET line-of-response data collected from the reconnaissance scan and surview CT image is used to determined the optimal acquisition and reconstruction parameters for the patient being scanned depending on the patient's anatomic region (brain, heart, lungs, general body), age (infant or adult) weight or BMI (to distinguish bariatric and normal cases) and the like. The reconnaissance scan preferably involves scanning the patient spanning the full region of the patient to be examined. For example, if it is determined from the data collected from the reconnaissance scan and surview CT that the patient is overweight, the imaging acquisition and control unit will increase the number of counts during acquisition in order to optimize scan acquisition. Likewise, other reconstruction parameters can be varied based on the reconnaissance scan and surview CT data in order optimize scan acquisition. Additionally, for example, if it is determined from the data collected from the reconnaissance scan and surview CT that the anatomical region of the patient being scanned is the brain, the PET reconstruction processor will optimize the reconstruction parameters to take into account the anatomical region being scanned to generate a higher resolution image. It is also contemplated that the data from the reconnaissance scan and surview CT is utilized to optimize the criteria for determining the time per region using the noise equivalent count rate (NECR), singles rate, total attenuation, and the like. The actual time required for the second pass can be reduced by reusing the data acquired from the reconnaissance scan. The reconstruction parameters can similarly vary by region. For example, the PET imaging system utilizes the data collected from the reconnaissance scan, the surview CT scan, and the targeted scan to generate a final image.

After determining the optimal acquisition and reconstruction parameters for the patient being scanned, the imaging acquisition and control unit 42 controls the PET radiation detectors 34 to collect the PET line-of-response data for the targeted scan according those parameters. During the targeted scan, the imaging acquisition and control unit 42 controls the PET radiation detectors 34 collect the PET line-of-response data in a continuous list-mode acquisition manner. The continuous acquisition speed, time per region, and the like varies based on reconnaissance scan and surview CT information. It is also contemplated that the reconnaissance and/or targeted scans do not need to be continuous and can vary time instead of speed such as a step and shoot acquisition manner. The targeted scan targets potentially non-contiguous regions thereby potentially reducing the dose required for CT. The regions can be defined purely from empirical data obtained from the reconnaissance scan and CT surview, as well as operator input defining particular regions. For example, the targeted scan enables multiple types of studies to be produced from a single acquisition (for example, brain, cardiac, whole body). In other words, the targeted scan involves scanning the patient over particular portions or regions of the patient thereby reducing the actual time required for the targeted scan.

The adaptive two-pass list-mode PET acquisition and reconstruction scheme enables feedback from the reconnaissance scan as well as other study information such as CT image data to drive targeted image acquisition and reconstruction. In other words, feedback from the reconnaissance scan drives the targeted or final image acquisition and reconstruction. It is also contemplated that such a scheme enables different portions of the patient to be scanned and reconstructed differently and enables the acquisition time to be allocated (or adjusted dynamically) where required. Thus, image quality can be improved by acquiring more data where need, and both acquisition and performance time can be reduced when not as much data is required. It is should also be appreciated that multiple studies can be obtained from a single two-pass acquisition; thereby reducing the time a patient needs to be on the table. It is common to perform multiple studies of a patient with the same injection; for example, a whole-body study and a brain scan. The standard practice would require two separate acquisitions and reconstructions. The adaptive two-pass acquisition and reconstruction scheme changes the amount of time associated with a targeted region (which translates into table speed with continuous acquisition). Using the aforementioned example of whole-body and brain, more data would be acquired for the brain region but only a subset of the data for the brain region would be used in the whole-body reconstruction to provide image quality results consistent with a uniform acquisition (and it would also reconstruct faster). It is also contemplated that data obtained from the initial reconnaissance scan is integrated with data obtained during the region-based scan; thereby reducing the amount of data that needs to be obtained during the region-based scan (and performance time).

It is also contemplated that the adaptive two-pass acquisition and reconstruction scheme determines the optimal acquisition and reconstruction parameters according to patient history, hospital specialty, physician preference, contrast agent, region of interest at optimal uptake time, body mass index, sex, and the like. For example, if the attending physician has a preference with regard to the image reconstruction, the two-pass acquisition and reconstruction scheme will adjust the acquisition and reconstruction parameters to fit the physician's preferences. Further, the two-pass acquisition and reconstruction scheme adjusts the acquisition and reconstruction parameters based on the injected contract agent, patient body mass index, and the like to optimize the image quality.

Additionally, it is also contemplated that data acquired during the reconnaissance scan and CT surview are utilized by the reconstruction processor to enhance the targeted PET image representation.

The one or more PET images are analysed to determine if and where detailed anatomical information is beneficial for the diagnosis of the patient. If it is determined that detailed anatomical information is beneficial for the diagnosis, the imaging acquisition and control unit 42 controls the patient support 36 to position the patient or subject into the first examination region 18 and controls the x-ray tube 24 and cooperating x-ray detector array 20 (components disposed in the CT scanner 12) to generate and acquire localization or diagnostic CT projection data according to the optimal acquisition parameters determined by the reconnaissance scan and the surview CT image. To reduce patient dose, the localization or diagnostic scan is limited to the targeted region. The acquired localization or diagnostic CT projection data is temporarily stored in a data buffer 50 and reconstructed by a CT reconstruction processor 52 to generate one or more localization or diagnostic CT images that are stored in a CT images memory 56.

A fusion processor 66 aligns, registers, or fuses the attenuation correction PET image representation and the localization or diagnostic high resolution CT image representation(s) and, in some embodiments, the low resolution x-ray image to generate a fused image. The individual images and the fused image are displayed on a display 76 e.g. of a computer 74. The attenuation corrected PET image representation, fused images, and others, are displayed on the display 76. The display also includes an input device 78 which a clinician can use for controlling the imaging system to select scanning sequences and protocols, fused image combinations, and the like. The graphic user interface also displays pre-corrected and corrected images concurrently for verification and/or further manual correction.

The imaging acquisition and control unit 42 are suitably embodied by a digital processor or controller, or by a combination of digital processors or controllers, operating in combination with suitable electronics, power supplies, and so forth configured to operate the x-ray tube 24 and radiation detector arrays 20, to operate a rotational mechanism that revolves the x-ray tube around the subject within the CT scanner 12, and so forth. The image analysis unit 64 is suitably embodied by a digital processor or controller optionally in combination with dedicated imaging acquisition and control hardware embodied, for example, as application-specific integrated circuitry (ASIC) hardware. The reconstruction processors 52, 60 are suitably embodied by a digital processor or controller, or by a combination of digital processors or controllers, optionally in combination with dedicated reconstruction pipeline hardware embodied, for example, as application-specific integrated circuitry (ASIC) hardware. A user interface, such as the illustrated computer 74, is provided to enable a radiologist or other user to configure, initiate, and monitor CT and PET imaging sessions, and to enable the radiologist or other user to view the resulting CT and/or PET images. The illustrated computer 74 includes a display 76, which may be embodied as a cathode-ray tube (CRT) display, a liquid crystal device (LCD) display, a plasma display, an organic light emitting device (OLED) display, or so forth. The computer 74 also includes a keyboard 78; however, additional or other input devices (not shown) may also be included such as a trackpad, a trackball, a touch-sensitive matrix coincident with the display 76 to define a touch-sensitive screen, or so forth. In some embodiments, some user interfacing functionality may be integrated with the CT scanner 12 and/or the PET scanner 26 as a built-in LCD display, built-in keypad, or so forth.

Figure 2:
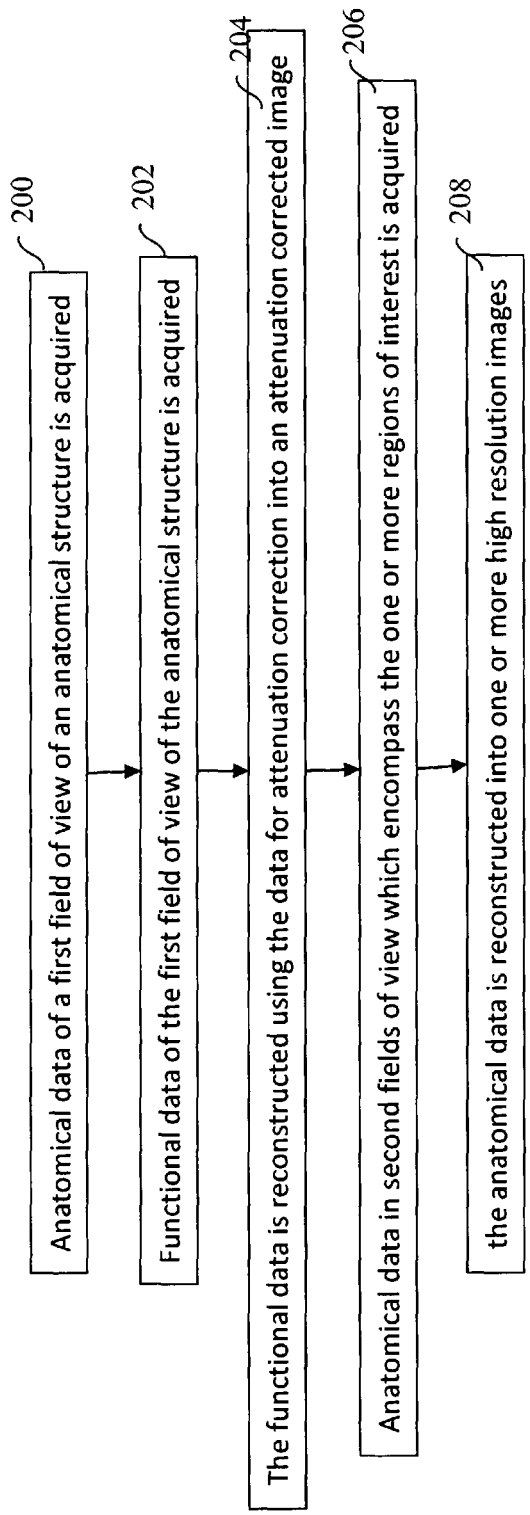
FIG. 2 is a diagrammatic illustration of a hybrid imaging scan procedure in accordance with the present application.

With reference to FIG. 2, a hybrid imaging scan procedure is illustrated. In a step 200, anatomical data of a first field of view of an anatomical structure is acquired. In a step 202, functional data of the first field of view of the anatomical structure is acquired. In a step 204, the functional data is reconstructed using the data for attenuation correction into an attenuation corrected image. In one embodiment, the functional data is acquired in a two-pass list-mode acquisition scheme. In a step 206, anatomical data in second fields of view which encompass the one or more regions of interest is acquired. The second fields of view being smaller than and confined in the first field of view. In a step 208, the anatomical data is reconstructed into one or more high resolution images.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A hybrid imaging system comprising:
   a first imaging system configured to acquire anatomical data of a first field of view of an anatomical structure;
   a second imaging system configured to acquire functional data of the anatomical structure;
   an imaging acquisition and control unit comprising a digital processor or controller configured to operate the first imaging system to acquire anatomical data and to operate the second imaging system to acquire functional data in a two-pass list-mode acquisition scheme including a first-pass list-mode acquisition that acquires first-pass functional data followed by a second-pass list-mode acquisition that acquires second-pass functional data wherein the second-pass list-mode acquisition is configured based on the first-pass functional data; and
   a reconstruction processor comprising electronics configured to reconstruct the functional data based on attenuation data generated from the anatomical data into an attenuation corrected image and reconstruct the anatomical data into one or more high resolution images of one or more regions of interest.

2. The hybrid imaging system according to claim 1, wherein the first-pass list-mode acquisition includes a reconnaissance scan, the reconstruction processor reconstructing first-pass functional data from the reconnaissance scan into a reconnaissance image, and the second-pass list-mode acquisition includes a targeted scan which is configured based on the reconnaissance image.

3. The hybrid imaging system according to claim 2, wherein the targeted scan acquires second-pass functional data of the one or more regions of interest.

4. The hybrid imaging system according to claim 3, wherein during the targeted scan, a patient having the anatomical structure moves relative the second imaging system at a non-constant speed, moving more slowly when acquiring second-pass functional data from the one or more of the regions of interest.

5. The hybrid imaging system according to claim 3, wherein during the targeted scan, a patient having the anatomical structure and second imaging modality move intermittently relative to each other with the motion stopping longer when second-pass functional data is being acquired from the one or more regions of interest.

6. The hybrid imaging system according to claim 2, wherein the reconnaissance scan acquires first-pass functional data in the first field of view of the anatomical structure.

7. The hybrid imaging system according to claim 1, wherein first-pass functional data acquired by the first-pass list-mode acquisition is utilized to configure optimal acquisition parameters for the second-pass list-mode acquisition.

8. The hybrid imaging system according to claim 1, wherein:
the first imaging system includes a computed tomography (CT) imaging system; and
the second imaging system includes a positron emission tomography (PET) imaging system.

9. The hybrid imaging system according to claim 1, wherein the reconstruction processor is further configured to fuse the attenuation corrected image and the one or more high resolution anatomical images together to generate a fused image.

10. The hybrid imaging system according to claim 9, wherein the fused image includes anatomical information covering the one or more regions of interest.

11. A hybrid imaging system comprising:
a computed tomography (CT) imaging system configured to acquire attenuation data of a first field of view of an anatomical structure;
a positron emission tomography (PET) imaging system configured to acquire first list mode data in a first pass;
a reconstruction processor configured to reconstruct the first list mode data based on the attenuation data into an attenuation corrected image;
wherein the PET imaging system is further configured to acquire second list mode data in a second pass with acquisition parameters of the second pass configured based on the first list mode data; and
wherein the reconstruction processor is further configured to reconstruct the attenuation corrected image and the second list mode data into a final attenuation corrected image.

12. A hybrid imaging system comprising:
a computed tomography (CT) or magnetic resonance (MR) imaging system;
a positron emission tomography (PET) or single photon emission computed tomography (SPECT) imaging system; and
electronics programmed to:
control the CT or MR imaging system to acquire CT or MR data;
control the PET or SPECT imaging system to perform a first-pass acquisition to acquire first-pass functional data; and
control the PET or SPECT imaging system to perform a second-pass acquisition configured based on the first-pass functional data to acquire second-pass functional data.

13. The hybrid imaging system of claim 12 wherein the electronics are programmed to control the PET or SPECT imaging system to perform the second-pass acquisition configured based on the first-pass functional data and further based on the CT or MR data to acquire second-pass functional data.

14. The hybrid imaging system of claim 13 wherein the electronics are further programmed to:
reconstruct the first-pass functional data using the CT or MR data for attenuation correction to generate a first-pass attenuation corrected image;
wherein the second-pass acquisition is configured based on the first-pass attenuation-corrected image.

15. The hybrid imaging system of claim 12 wherein the electronics are further programmed to:
reconstruct at least the second-pass functional data to generate one or more functional images.

16. The hybrid imaging system of claim 15 wherein the electronics are programmed to reconstruct both the first-pass functional data and the second-pass functional data to generate the one or more functional images.

17. The hybrid imaging system of claim 15 wherein the electronics are further programmed to:
control the CT or MR imaging system to acquire targeted CT or MR data for a region identified in the one or more functional images; and
reconstruct the targeted CT or MR data to generate one or more high resolution CT or MR images.

* * * * *